United States Patent
Atkins

(10) Patent No.: US 7,939,571 B2
(45) Date of Patent: May 10, 2011

(54) PROCESS FOR THE CONVERSION OF SYNTHESIS GAS TO OXYGENATE

(75) Inventor: Martin Philip Atkins, Ashford (GB)

(73) Assignee: BP Chemicals Limited, Middlesex (GB)

( * ) Notice: Subject to any disclaimer, the term of this patent is extended or adjusted under 35 U.S.C. 154(b) by 89 days.

(21) Appl. No.: 11/920,750

(22) PCT Filed: May 18, 2006

(86) PCT No.: PCT/GB2006/001821
§ 371 (c)(1),
(2), (4) Date: Nov. 20, 2007

(87) PCT Pub. No.: WO2006/123146
PCT Pub. Date: Nov. 23, 2006

(65) Prior Publication Data
US 2009/0124710 A1    May 14, 2009

(30) Foreign Application Priority Data
May 20, 2005    (GB) .................................. 0510356.9

(51) Int. Cl.
C07C 27/06    (2006.01)
(52) U.S. Cl. ...................................................... 518/716
(58) Field of Classification Search .................. 568/880; 518/716
See application file for complete search history.

(56) References Cited

U.S. PATENT DOCUMENTS

| 4,224,236 | A | | 9/1980 | Wunder et al. | |
|---|---|---|---|---|---|
| 4,408,080 | A | * | 10/1983 | Isogai et al. ................. | 568/484 |
| 4,670,473 | A | * | 6/1987 | Walker et al. ................. | 518/706 |
| 4,752,623 | A | | 6/1988 | Stevens et al. | |
| 5,385,949 | A | | 1/1995 | Tierney et al. | |
| 6,284,217 | B1 | | 9/2001 | Wang et al. | |
| 6,346,555 | B1 | | 2/2002 | Luo et al. | |
| 6,500,781 | B2 | | 12/2002 | Luo et al. | |
| 2002/0037938 | A1 | | 3/2002 | Luo et al. | |
| 2005/0107482 | A1 | | 5/2005 | Van Egmond et al. | |

FOREIGN PATENT DOCUMENTS

| DE | 25 03 204 | | 7/1975 |
|---|---|---|---|
| EP | 0 010 295 | A1 | 4/1980 |
| EP | 0 033 212 | | 8/1981 |
| EP | 0 079 132 | A1 | 5/1983 |
| EP | 0 180 719 | | 5/1986 |
| EP | 0 303 438 | A2 | 2/1989 |
| EP | 550 242 | | 12/1992 |
| GB | 1 413 929 | | 11/1975 |
| JP | 61-178933 | A | 8/1986 |
| JP | 62-148437 | A | 7/1987 |
| JP | 62-148438 | A | 7/1987 |
| JP | 01-294643 | A | 11/1989 |
| WO | WO 99/02254 | A1 | 1/1999 |
| WO | WO 00/23689 | A1 | 4/2000 |

OTHER PUBLICATIONS

Beretta, Alessandra, "Development of a Process for Higher Alcohol Production via Synthesis Gas", Ind. Eng. Chem. Res, vol. 37, pp. 3896-3908, (1998).
International Search Report mailed Feb. 27, 2007.
PCT Written Opinion of the International Searching Authority dated Feb. 27, 2007.
PCT International Preliminary Report on Patentability completed Jun. 19, 2007.
PCT Demand dated Jun. 13, 2007.
*Chemical Encyclopedia*, vol. 1 and 4, editor in chief N.S. Zefirow, Moscow (1995).
Gunardson, H.H., et al; "Produce CO-rich synthesis gas"; *Hydrocarbon Processing*; vol. 78 No. 4, pp. 87-90, 92-93 (Apr. 1999).
Bourbonneux, G.erard; "Fisher-Tronsch synthesis gas production routes"; *Petrole et Techniques*; No. 415, pp. 86-93 (Jul.-Aug. 1998).
Mayer, J., et al; "A Microstructured Reactor for the Catalytic Partial Oxidation of Methane to Syngas"; *IMRET 3: Proceedings of the Third International Conference on Microreaction Technology*; Editor W. Ehrfeld, Springer Verlag, pp. 187-196 (1999).
*Hydrocarbon Engineering*; vol. 5, No. 5, pp. 67-69 (2000).
*Hydrocarbon Processing*; vol. 79, No. 9, 34 (Sep. 2000).
*Today's Refinery*; vol. 15, No. 8 9 (Aug. 2000).
Weissermel, K. and Arpe H.-J.; *Industrial Organic Chemistry*, Second, Revised and Extended Edition, pp. 19-21 (1993).

* cited by examiner

*Primary Examiner* — Brian J Davis
(74) *Attorney, Agent, or Firm* — Nixon & Vanderhye

(57) ABSTRACT

Process for the conversion of carbon oxide(s) and hydrogen-containing feedstocks to C2-oxygenates in the presence of a particulate catalyst, by reacting carbon oxide(s) and hydrogen in the presence of a particulate rhodium-based catalyst in a conversion reactor to form C2-oxygenates. A saturated monocarboxylic acid having from 1 to 3 carbon atoms and/or an ester of a saturated monocarboxylic acid having from 1 to 3 carbon atoms with a monohydiic aliphatic paraffinic alcohol having from 1 to 4 carbon atoms are separated from the ethanol and acetaldehyde produced in the conversion reactor and is/are sent back to the conversion reactor.

9 Claims, No Drawings

PROCESS FOR THE CONVERSION OF SYNTHESIS GAS TO OXYGENATE

This application is the U.S. national phase of International Application No. PCT/GB2006/001821 filed 18 May 2006 which designated the U.S. and claims priority to GB 0510356.9 filed 20 May 2005, the entire contents of each of which are hereby incorporated by reference.

The present invention relates to an improved process for the conversion of carbon oxide(s) and hydrogen containing feedstocks to oxygen containing hydrocarbon compounds in the presence of a particulate catalyst.

In particular, the present invention relates to an improved process for the conversion of carbon oxide(s) (CO and CO2) and hydrogen containing feedstocks, e.g. synthesis gas or syngas, to C2-oxygenates in the presence of a particulate rhodium-based catalyst.

BACKGROUND OF THE INVENTION

EP-A-0 010 295 describes a process for preparing ethanol from synthesis gas, in which the reaction is carried out over a supported rhodium catalyst comprising, as cocatalyst, one or more of the elements zirconium, hafnium, lanthanum, platinum, chromium and mercury.

EP-A-0 079 132 relates to a process for preparing oxygenated hydrocarbons by catalytic reaction of synthesis gas over a supported catalyst comprising, as active components, rhodium, silver, zirconium and molybdenum and also, if desired, iron, manganese, rhenium, tungsten, ruthenium, chromium, thorium and potassium. The preferred support material is silicon dioxide.

JP 62/148437 and JP 62/148438 disclose the simultaneous production of acetic acid, acetaldehyde and ethanol from a synthesis gas reacted in the presence of a rhodium catalyst pretreated with sulfur-containing compounds. JP 61/178933 discloses producing oxygenates from a synthesis gas wherein the reaction is carried out in the presence of a rhodium catalyst provided with an accelerator metal such as scandium, iridium or an alkali earth metal. JP01/294643 discloses the production of oxygenated compounds such as acetic acid in which a synthesis gas is reacted in the presence of a rhodium catalyst on a silica substrate.

U.S. Pat. No. 6,346,555 and U.S. Pat. No. 6,500,781 disclose a catalyst and a process for preparing C2-oxygenates by reaction of CO and H2 over a rhodium-containing supported catalyst, in which the catalyst consists essentially of rhodium, zirconium, iridium, at least one metal selected from amongst copper, cobalt, nickel, manganese, iron, ruthenium and molybdenum, and at least one alkali metal or alkaline earth metal selected from amongst lithium, sodium, potassium, rubidium, magnesium and calcium, on an inert support

SUMMARY OF THE INVENTION

It is an object of the present invention to provide an improved process in term of selectivity and catalyst activity and operating life for the conversion of carbon oxide(s) and hydrogen containing feedstocks to oxygen containing hydrocarbon compounds in the presence of a particulate catalyst.

In particular, the present invention relates to an improved process in term of selectivity and catalyst activity and operating life for the conversion of carbon oxide(s) and hydrogen containing feedstocks, e.g. synthesis gas or syngas, to C2-oxygenates in the presence of a particulate rhodium-based catalyst.

The present invention thus provides a process for the conversion of carbon oxide(s) and hydrogen containing feedstocks to oxygen containing hydrocarbon compounds in the presence of a particulate catalyst comprising the step of reacting carbon oxide(s) and hydrogen in the presence of a particulate catalyst in a conversion reactor to form oxygen containing hydrocarbon compounds characterised in that a saturated monocarboxylic acid having from 1 to 3 carbon atoms and/or an ester of a saturated monocarboxylic acid having from 1 to 3 carbon atoms with a monohydric aliphatic paraffinic alcohol having from 1 to 4 carbon atoms are added to the conversion reactor.

In particular, the present invention provides a process for the conversion of carbon oxide(s), preferably carbon monoxide and hydrogen containing feedstocks, e.g. synthesis gas or syngas, to C2-oxygenates in the presence of a particulate rhodium-based catalyst comprising the step of reacting carbon oxide(s) and hydrogen in the presence of said particulate rhodium-based catalyst in a conversion reactor to form C2-oxygenates characterised in that a saturated monocarboxylic acid having from 1 to 3 carbon atoms and/or an ester of a saturated monocarboxylic acid having from 1 to 3 carbon atoms with a monohydric aliphatic paraffinic alcohol having from 1 to 4 carbon atoms are added to the conversion reactor

DETAILED DESCRIPTION OF PREFERRED EMBODIMENTS

According to a preferred embodiment, the present invention provides a process for the conversion of hydrocarbon to C2-oxygenates comprising the steps of
1. converting hydrocarbon to a mixture of carbon oxide(s), preferably carbon monoxide, and hydrogen in a syngas reactor,
2. passing the mixture of carbon oxide(s) and hydrogen from the syngas reactor to a conversion reactor, and
3. reacting said mixture in said conversion reactor in the presence of a particulate rhodium-based catalyst to form C2-oxygenates, characterised in that a saturated monocarboxylic acid having from 1 to 3 carbon atoms and/or an ester of a saturated monocarboxylic acid having from 1 to 3 carbon atoms with a monohydric aliphatic paraffinic alcohol having from 1 to 4 carbon atoms are added to the conversion reactor.

For the purpose of the present invention and appended claims, producing oxygen containing hydrocarbon compounds from synthesis gas means that the hydrocarbon oxygenates represent at least 50% by weight of the products obtained from the conversion reactor, preferably at least 55% by weight, more preferably at least 60% by weight.

According to a preferred embodiment of the present invention, the C2-oxygenates are mainly ethanol, acetaldehyde and acetic acid; said ethanol, acetaldehyde and acetic acid preferably represent together at least 50% by weight of the products obtained from the conversion reactor, more preferably at least 55% by weight, most preferably at least 60% by weight.

According to another preferred embodiment of the present invention, water is also produced in the conversion reactor; then, water, ethanol, acetaldehyde and acetic acid preferably represent together at least 80% by weight of the products obtained from the conversion reactor, more preferably at least 90% by weight, most preferably at least 95% by weight.

According to a preferred embodiment of the present invention, the crude products from the conversion reactor contains about from 30 to 40% by weight of water and 55 to 70% by weight of C2-oxygenates. The C2-oxygenates feed then preferably comprises about 26 to 40% by weight of acetic acid, about 26 to 40% by weight of acetaldehyde and about 26 to 40% by weight of ethanol.

In one variant, the crude product is subjected to a "flash" distillation in which most of the acetaldehyde and ethanol is flashed overhead with some of the water and the remaining acetic acid is left at the bottom of the column (with water). This bottom stream contains about 90% by weight of the acetic acid and about 90% by weight of the water from the crude products, i.e. a bottom stream composition which represents about 50% by weight of the crude products.

According to a preferred embodiment of the present invention, the saturated monocarboxylic acid having from 1 to 3 carbon atoms and/or the ester of a saturated monocarboxylic acid having from 1 to 3 carbon atoms with a monohydric aliphatic paraffinic alcohol having from 1 to 4 carbon atoms which are added to the conversion reactor comes from the oxygenates obtained from the conversion reactor.

Said saturated monocarboxylic acid having from 1 to 3 carbon atoms and/or ester of a saturated monocarboxylic acid having from 1 to 3 carbon atoms with a monohydric aliphatic paraffinic alcohol having from 1 to 4 carbon atoms are thus preferably separated from the ethanol and acetaldehyde produced in the conversion reactor and sent back to the said conversion reactor.

According to another preferred embodiment of the present invention, the saturated monocarboxylic acid having from 1 to 3 carbon atoms and/or the ester of a saturated monocarboxylic acid having from 1 to 3 carbon atoms with a monohydric aliphatic paraffinic alcohol having from 1 to 4 carbon atoms which are added to the conversion reactor are preferably selected from acetic acid, methyl acetate or ethyl acetate or a mixture thereof.

Quite surprisingly, the addition and/or recycle of even tiny amounts of the acids and/or esters to the conversion reactor have proven to be highly beneficial to the C2-oxygenates selectivity, especially the ethanol selectivity, while simultaneously increasing catalyst activity and improving operating life.

Preferably, the rhodium catalyst used in the present invention is a rhodium catalyst supported on a micro-porous silica, said micro-porous silica preferably having a BET specific surface area of 150 to 350 m2/g, preferably 150 to 349 m2/g preferably 200 to 300 m2/g, an average pore size of 100 to 300 Å, preferably 101 to 300 Å, preferably 150 to 250 Å and a pore volume of 0.5 to 1.5 ml/g, preferably 0.9 to 1.1 ml/g.

The BET surface area, average pore size and pore volume have been obtained by Micromeritics ASAP 2010 and N2 adsorption-desorption technique.

referably, the rhodium catalyst used in the present invention is a rhodium catalyst supported on a micro-porous silica consisting of components Rh—Mn—Fe—M1-M2 supported on silica wherein M1 can be Li and/or Na and M2 can be Ru and/or Ir, wherein Rh is 0.1 to 3%, preferably 0.3 to 2%, by weight based on the total catalyst weight and the weight ratio of Mn/Rh is 0.5-12, the weight ratio of Fe/Rh is 0.01-0.5, the weight ratio of M1/Rh is 0.04-0.2, and the weight ratio of M2/Rh is 0.1-1.0.

Processes for producing mixtures of carbon monoxide and hydrogen (synthesis gas) are well known. Each has its advantages and disadvantages and the choice of using a particular reforming process is dictated by economic and available feed stream considerations, as well as by the desired mole ratio of H2:CO in the feedstock resulting from the reforming reaction. The synthesis gas may be prepared using any of the processes known in the art including partial oxidation of hydrocarbons, steam reforming, gas heated reforming, microchannel reforming (as described in, for example, U.S. Pat. No. 6,284,217 which is herein incorporated by reference), plasma reforming, autothermal reforming and any combination thereof A discussion of these synthesis gas production technologies is provided in "Hydrocarbon Processing" V78, N.4, 87-90, 92-93 (April 1999) and "Petrole et Techniques", N. 415, 86-93 (July-August 1998). It is also envisaged that the synthesis gas may be obtained by catalytic partial oxidation of hydrocarbons in a microstructured reactor as exemplified in "IMRET 3: Proceedings of the Third International Conference on Microreaction Technology", Editor W Ehrfeld, Springer Verlag, 1999, pages 187-196. Alternatively, the synthesis gas may be obtained by short contact time catalytic partial oxidation of hydrocarbonaceous feedstocks as described in EP 0303438. Preferably, the synthesis gas is obtained via a "Compact Reformer" process as described in "Hydrocarbon Engineering", 2000, 5, (5), 67-69; "Hydrocarbon Processing", 79/9, 34 (September 2000); "Today's Refinery", 15/8, 9 (August 2000); WO 99/02254; and WO 200023689.

Any hydrocarbon-containing feed stream that can be converted into a feedstock comprising carbon monoxide and hydrogen, most preferably a synthesis gas (or "syngas"), is useful in the processes of the invention. The ratio of hydrogen to carbon monoxide in the reaction zone is preferably in the range of 20:1 to 0.1:1 by volume, more preferably in the range of 5:1 to 1:1, most preferably in the range of 2.5:1 to 1.5:1, e.g. 2:1. Useful feed streams include natural gas (mainly methane, but natural gas composition can vary depending on location and source), naphtha, refinery off-gas, LPG, gas oil, vacuum residuals, shale oils, asphalts, various types of fuel oils, coal based/lignin deposits and hydrocarbon containing process recycle streams. According to a preferred embodiment of the present invention, methane is used as the hydrocarbon-containing feed stream to be converted into CO and H2.

Feedstocks comprising carbon monoxide and hydrogen, e.g., synthesis gas, may undergo purification prior to being fed to any reaction zones. For use in the processes of this invention, the synthesis gas should ideally be essentially free of catalyst poisons and inhibitors such as hydrogen sulfide, carbonyl sulfide, metal carbonyls, e.g., iron carbonyl and nickel carbonyl, ammonia, basic organic compounds, e.g., methyl amine and ethyl amine, and generally any compounds that will neutralize an acid. Synthesis gas purification may be carried out by processes known in the art. See, for example, Weissermel, K. and Arpe H.-J., Industrial Organic Chemistry, Second, Revised and Extended Edition, 1993, pp. 19-21.

The particular reaction conditions for the conversion reactor embodiments described below are not narrowly critical and can be any effective reaction conditions sufficient to produce mainly oxygen containing hydrocarbon compounds. The exact reaction conditions will be governed by the best compromise between achieving high catalyst selectivity, activity, lifetime and ease of operability, as well as the intrinsic reactivity of the starting materials in question and the stability of the starting materials and the desired reaction product to the reaction conditions.

In one embodiment of this invention, feedstock comprising the desired molar ratio of H2:CO is fed to a conversion reactor at a controlled rate and the reaction is carried out in a reaction zone under controlled conditions of temperature and pressure in the presence of a catalyst to convert the feedstock into oxygenates. The temperature in the reaction zone is selected from the range of from about 150° C. to about 400° C., preferably a temperature in the range of from about 200° C. to about 350° C. The gas hourly space velocity (GHSV) of the feedstock (liters of feedstock/hr/liter of catalyst) passing through the reaction zone can vary significantly, depending upon a variety of factors such as, for example, reaction conditions, composition of the feedstock and quantity and type of catalyst being used. The GHSV can be maintained at any rate in the range of from about 1 to about 30,000 hr-1 or more, preferably will be maintained at a rate of at least about 500 hr-1, and more preferably will be maintained at a rate of at least 1,000 hr-1. The pressure in the conversion reaction zone may be selected from the range of from about 5 to 200 bar, preferably a pressure in the range of from about 25 to 120 bar. The hydrogen and carbon monoxide partial pressures should be sufficient to enable the production of oxygenates. Hydrogen and carbon monoxide may be fed separately to the conversion reactor or, preferably in combination, e.g., as synthesis gas.

For purposes of this invention, GHSV is gas hourly space velocity which is the rate of gas flow over the catalyst. It is determined by dividing the volume of gas (at 25° C. and 1 atmosphere) which passes over the catalyst in one hour by the volume of the catalyst. LHSV is liquid hourly space velocity which is the rate that the liquid organic substrate is fed to the conversion reactor. It is determined by dividing the liquid volume pumped in one hour by the volume of catalyst.

The conversion to oxygenates reaction can be carried out by passing the mixture of hydrogen and carbon monoxide over the rhodium-based catalyst as a vapor phase reaction or as a liquid phase reaction, e.g., slurry reaction.

The reaction may be carried out in any appropriate reactor, e.g. a tubular reactor using a fixed bed of the catalyst. The reactants may be fed to the catalyst by feeding down or up, or a combination of both, to a fixed bed located in a tubular reactor. It may be desirable to use a reactor design that operates by plug flow and causes minimal turbulence in the reactor zone. The reaction may be effected in a dynamic bed of the catalyst. In such a reaction, the bed of catalyst is moving such as in the case of a fluid bed of the catalyst.

The invention claimed is:

1. Process for the conversion of carbon oxide(s) and hydrogen-containing feedstocks to C2-oxygenates in the presence of a particulate catalyst comprising the step of reacting carbon oxide(s) and hydrogen in the presence of a particulate rhodium-based catalyst in a conversion reactor to form C2-oxygenates, wherein a saturated monocarboxylic acid having from 1 to 3 carbon atoms and/or an ester of a saturated monocarboxylic acid having from 1 to 3 carbon atoms with a monohydric aliphatic paraffinic alcohol having from 1 to 4 carbon atoms are separated from the ethanol and acetaldehyde produced in the conversion reactor and is/are sent back to said conversion reactor.

2. Process according to claim 1 wherein the carbon oxide (s) and hydrogen containing feedstocks are synthesis gas or syngas.

3. Process for the conversion of hydrocarbon to C2-oxygenates comprising the steps of:
a. converting hydrocarbon to a mixture of carbon oxide(s) and hydrogen in a syngas reactor,
b. passing the mixture of carbon oxide(s) and hydrogen from the syngas reactor to a conversion reactor, and
c. reacting said mixture in said conversion reactor in the presence of a particulate rhodium-based catalyst to form C2-oxygenates, wherein a saturated monocarboxylic acid having from 1 to 3 carbon atoms and/or an ester of a saturated monocarboxylic acid having from 1 to 3 carbon atoms with a monohydric aliphatic paraffinic alcohol having from 1 to 4 carbon atoms are separated from the C2-opxygenates produced in the conversion reactor and is/are sent back to said conversion reactor.

4. Process according to claim 1 wherein the C2-oxygenates comprise ethanol, acetaldehyde and acetic acid, and said ethanol, acetaldehyde and acetic acid together represent at least 50% by weight of the products obtained from the conversion reactor.

5. Process according to claim 1 wherein the saturated monocarboxylic acid having from 1 to 3 carbon atoms and/or the ester of a saturated monocarboxylic acid having from 1 to 3 carbon atoms with a monohydric aliphatic paraffinic alcohol having from 1 to 4 carbon atoms which are added to the conversion reactor are selected from acetic acid, methyl acetate or ethyl acetate or a mixture thereof.

6. Process according to claim 1 wherein the conversion of carbon oxide(s) and hydrogen in the conversion reactor in the presence of a particulate rhodium-based catalyst to form C2-oxygenates is carried out as a vapour phase reaction.

7. Process according to claim 4, wherein the C2-oxygenates comprise ethanol, acetaldehyde and acetic acid, and said ethanol, acetaldehyde and acetic acid and together represent at least 55% by weight of the products obtained from the conversion reactor.

8. Process according to claim 4, wherein the C2-oxygenates comprise ethanol, acetaldehyde and acetic acid, and said ethanol, acetaldehyde and acetic acid together represent at least 60% by weight of the products obtained from the conversion reactor.

9. Process according to claim 3, wherein step a converts the hydrocarbon to carbon monoxide and hydrogen in the syngas reactor.

* * * * *